United States Patent

Loccufier et al.

[11] Patent Number: 5,989,774
[45] Date of Patent: Nov. 23, 1999

[54] PHOTOGRAPHIC MATERIAL CONTAINING A NEW HYDRAZIDE TYPE

[75] Inventors: Johan Loccufier, Zwijnaarde; Stefaan Lingier, Assenede; Paul Callant, Edegem; Sabine Emmers, Lommel, all of Belgium

[73] Assignee: Agfa-Gevaert, N.V., Mortsel, Belgium

[21] Appl. No.: 09/151,348

[22] Filed: Sep. 10, 1998

[30] Foreign Application Priority Data

Sep. 10, 1997 [EP] European Pat. Off. .............. 97202790

[51] Int. Cl.⁶ .......................... G03C 1/06; C07D 213/42; C07D 213/70; C07D 235/06
[52] U.S. Cl. ........................ 430/264; 430/598; 564/310; 564/81; 564/148
[58] Field of Search ..................... 430/264, 598; 564/310, 81, 148

[56] References Cited

U.S. PATENT DOCUMENTS 5,288,590  2/1994  Kuwabara et al. .................... 430/260

FOREIGN PATENT DOCUMENTS 0816913  7/1998  European Pat. Off. .......... G03C 1/06

6-175253  6/1994  Japan ................. G03C 1/06

*Primary Examiner*—Mark F. Huff
*Attorney, Agent, or Firm*—Breiner & Breiner

[57] ABSTRACT

A silver halide photographic material is disclosed containing a new type of hydrazide compound represented by following general formula I, the different symbols of which are defined in the description.

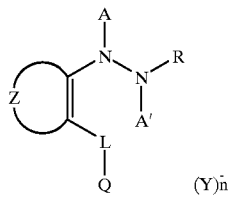

formula I

In a preferred embodiment Q is pyridinium, substituted with a propargyllic group or butynyl group.

The photographic material is preferably a graphic arts recording material. High gradation and excellent hard dot quality are obtained.

8 Claims, No Drawings

PHOTOGRAPHIC MATERIAL CONTAINING A NEW HYDRAZIDE TYPE

FIELD OF THE INVENTION

The present invention relates to photographic materials, especially graphic arts materials, giving rise to improved gradation and image quality.

BACKGROUND OF THE INVENTION

In graphic arts reproduction processes the original image appearing to have EL continuous tone gradation is reproduced by a collection of a large number of dots and/or lines, either by optical means in the case of a camera film, or by electronic means in case of a recorder film. The tone of the reproduced image is influenced by both the size of the dots and lines and their density. A graphic arts film exposed in a way to exactly render the relative proportions of black and white in the original must produce dots and lines of sufficient density; another reason herefore is the fact that no substantial amount of copying light may be transmitted through the dots and lines in a further duplicating cycle or during the direct exposure of a printing plate. Therefore a photographic element showing high contrast or so-called "lith gradation" on development is highly desired. Furthermore the generated or reproduced dots and lines must exhibit a well-shaped form and sharp edges.

This most desired combination of high contrast and excellent dot quality is commonly termed "lith quality". The goal of achieving optimal lith quality is reached by the combination of specially designed graphic arts material and appropriate processing systems. A 30 first group of such processing systems consists of the traditional "lith developers" characterized by the presence of hydroquinone as the sole developing agent and a low but critical sulphite ions content giving rise to an infectious development mechanism, as was described by Yule in *The Journal of the Franklin Institute,* Vol. 239, p. 221–223, (1945). This type of development is believed to proceed autocatalytically. The low concentration of sulphite is maintained by the progressive dissociation of an aldehyde-bisulphite adduct. However these conventional lith developers are rather instable in time and require complicated replenishment systems for both oxidation and exhaustion. Furthermore their developing capacity is limited due to the fact that they contain hydroquinone as the sole developing agent.

In more recent times so-called "hard dot Rapid Access" developers were introduced on the market which combine a good stability with a "lith quality" in the reproduction of lines and screen dots. Examples of such developers and corresponding appropriate photographic materials include the GRANDEX system, marketed by FUJI PHOTO ltd., AGFASTAR, marketed by AGFA-GEVAERT N.V. and the ULTRATEC system, marketed by EASTMAN KODAK Co. Some of these systems make use of the contrast promoting action, induced by a nucleating mechanism, of hydrazine derivatives known for long time in the photographic art. As described by Simson et al., U.S. Pat. No. 4,650,746, use of a hydrazine compound permits the use of an auxiliary development agent in combination with the hydroquinone type of developing agent so that the development capacity can be increased. It also permits the presence of a relatively high sulphite concentration in order to protect the developer against aerial oxidation and thereby prolonging its effective working life. Further early disclosures on hydrazine compounds, incorporated either in a photographic element or in a developing solution, include Smith U.S. Pat. No. 2,410,690, Stauffer U.S. Pat. No. 2,419,974, Trivelli U.S. Pat. No. 2,419,975 and Hunsberger U.S. pat. No. 2,892,715 and an article by Stauffer, Smith and Trivelli entitled "The influence of photographic developers containing hydrazine upon the characteristic curves of photographic materials", *The Journal of the Franklin Institute,* Vol. 238, p. 291–298, October 1944. Since then the photographic world has undertaken extensive research on hydrazine chemistry for use in photographic applications and the recent patent literature on new hydrazine derivatives and on the combination of known or new hydrazines with other useful ingredients in photographic elements or developers is abundant.

A practical early recognized problem was caused by the high pH levels needed for the developers containing hydrazine compounds or used with photographic elements containing these compounds in order to get the maximum effect on contrast. The teaching of Nothnagle U.S. Pat. No. 4,269,929 brought a solution to this problem. Here a method for high contrast development was disclosed involving a hydrazine compound, either in the photographic element or in the developer, said developer further containing a hydroquinone developing agent, a 3-pyrazolidinone developing agent, sulphite ions, and a "contrast-promoting amount" of an amino compound. In a preferred embodiment the hydrazine compound was incorporated in the photographic material. According to this patent, issued May 26, 1981, this particular combination of ingredients allow the use of a rather moderate alkaline pH for the developing solution while retaining the desired high contrast and dot quality characteristics. In this way an excellent combination of lith quality of the finished material, high developing capacity and long effective life of the developer was achieved.

Since then intense research has been conducted to improve the performance of hydrazines, mostly acylhydrazides, and in particular to make them workable in combination with conventional rapid access developers having a pH around 10.5 and containing no special ingredients such as amine boosters. Specific new hydrazide derivatives are described, e.g. in JP-A 57-99635, EP 0 217 310, JP-A 61-270744, JP-A 62-89958, EP 0 283 040, EP 0 301 799, U.S. Pat. No. 4,816,373, U.S. Pat. No. 4,847,180, JP-A 63-294552, JP-A 63-44649, JP-A 63-8715, EP 0 283 040, JP-A 01-100530, EP 0 345 025, JP-A 01-201650, EP 0 356 898, DE 38 29 078, U.S. Pat. No. 4,950,578, U.S. Pat. No. 5,028,510, EP 0 399 460, U.S. Pat. No. 5,006,445, JP-A 01-285940, U.S. Pat. No. 4,988,604, U.S. Pat. No. 4,994,365, JP-A 02-300474, JP-A 02-302750, JP-A 02-841, JP-A 02-947, EP 0 444 506, EP 0 479 156, JP-A 04-283743, EP 0 539 925 and U.S. Pat. No. 5,212,045.

A study on the nucleating mechanism of acylhydrazides, responsible for infectious development, can be find in Simson, *SPSE,* 25th Fall Symposium, (1985), p. 48. Other studies include Kitchin et al., J. Phot. SCi., Vol. 35, (1987), p. 162, Shinoara et al., *J. Photogr. Sci.,* Vol. 35, (1987), p. 181, and Kobayashi, *J. Phot. Sci.,* Vol. 43, (1995), p. 186.

An important technological breakthrough was the development and use of sulphonamido-arylhydrazides as disclosed in EP 0 286 840 and U.S. Pat. No. 5,104,769, which proved to be a very reactive and effective type. Another main progress was the use of hydrazides, especially sulphonamido-arylhydrazides in combination with so-called "incorporated boosters", such as disclosed in Machonkin U.S. Pat. No. 4,975,354, which can be incorporated into the photographic material itself instead of the developer. Still other graphic arts systems are based on the use of hydrazine types that can release a photographically useful group, e.g. an accelerator or a development restrainer, such as disclosed in e.g. EP 0 393 720, EP 0 393 721, EP 0 399 460, U.S. Pat. No. 5,258,259, EP 0 420 005, U.S. Pat. No. 5,252,438 and U.S. Pat. No. 5,262,274.

In European Patent Application, appl. No. 97201902 a new class of active arylhydrazides is disclosed having in ortho position a substituent comprising a pyridinium, quinolinium or isoquinolinium group. With this class of hydrazides high gradation was obtained. However, this type of hydrazides causes an important image spread leading to considerable dot growth in function of exposure intensity or time of development. In the case of a correct exposure of a 50% dot original this results in a poor quality of the small dots (5% or less).

The present invention extends the teachings on hydrazine compounds in photographic silver halide materials, and constitutes a further improvement to the teachings of European Patent Application, appl. No. 97201902, cited above.

OBJECTS OF THE INVENTION

It is an object of the present invention to provide a new class of reactive hydrazines for use in a photographic material.

It is a further object of the present invention to provide a photographic material, in particular a graphic arts recording material, showing high gradation, high maximal density, excellent quality of reproduced dot and line patterns, and restrained image spread, without the need for a special booster in the film or the developing solution.

SUMMARY OF THE INVENTION

The objects of the present invention are realized by providing a photographic material comprising a support, at least one emulsion layer, and optionally one or more other hydrophilic layers, characterized in that said emulsion layer or another hydrophilic layer adjacent to said emulsion layer contains a compound according to general formula I

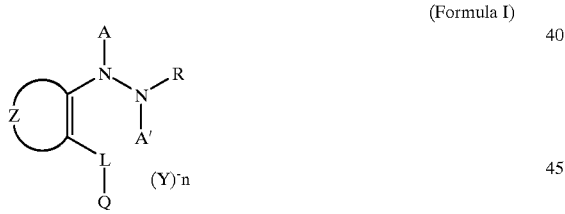

(Formula I)

or a dimeric form of said formula I, wherein

1) R represents an acyl-group selected from the group consisting of $COR^1$, $SO_2R^2$, $SOR^3$, $POR^4 R^5$ and $COCOR^6$; each of $R^1$ and $R^6$ independently represents hydrogen, a substituted or unsubstituted alkyl group, a substituted or unsubstituted aryl- or heteroarylgroup, $OR^7$, or $NR^8R^9$; each of $R^2$ and $R^3$ independently represents a substituted or unsubstituted alkylgroup, a substituted or unsubstituted aryl- or heteroarylgroup, OR or $NR^8R^9$; each of $R^4$ and $R^5$ indepedently represents one of the significances given for $R^2$ or they may constitute together the necessary atoms to close a ring; $R^7$ represents a substituted or unsubstituted alkylgroup, a substituted or unsubstituted aryl- or heteroarylgroup; each of $R^8$ and $R^9$ independently represents hydrogen, a substituted or unsubstituted alkylgroup or a substituted or unsubstituted aryl- or heteroarylgroup or they may constitute together the necessary atoms to form a ring;

2) each of A and A' independently represent a hydrogen, a group capable of yielding hydrogen under alkaline photographic processing conditions or a $SO_2R^{10}$-group, provided that, if A is a $SO_2R^{10}$, A' is a hydrogen and vice versa. $R^{10}$ has one of the significances given for $R^2$;

3) L is a divalent linking group;

4) Q is an aromatic heterocyclic ring containing a quaternary nitrogen atom which is substituted by a substituted or unsubstituted aliphatic chain comprising at least one carbon—carbon triple bond;

5) $Y^-$ is a negatively charged counterion to compensate the positive charge of Q;

n is 0 if the compound according to formula I is an inner salt or an integer equal to the positive charge of Q, and 6) Z represents the necessary atoms to form a substituted or unsubstituted aromatic or heteroaromatic ring.

In a most preferred embodiment Q is a pyridinium group bearing a propargyllic group.

DETAILED DESCRIPTION OF THE INVENTION

Typical examples of compounds according to the general formula the present invention are given below

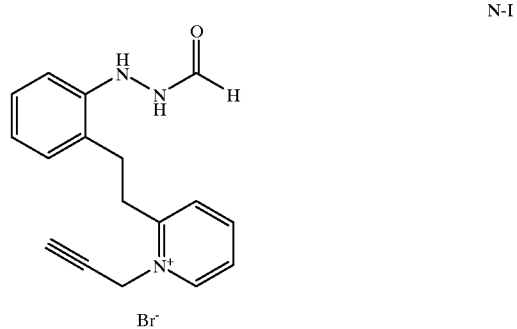

N-I

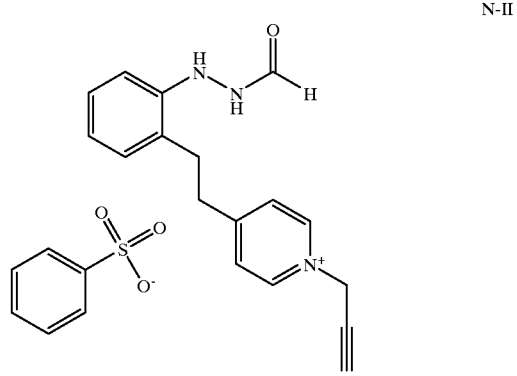

N-II

5
-continued
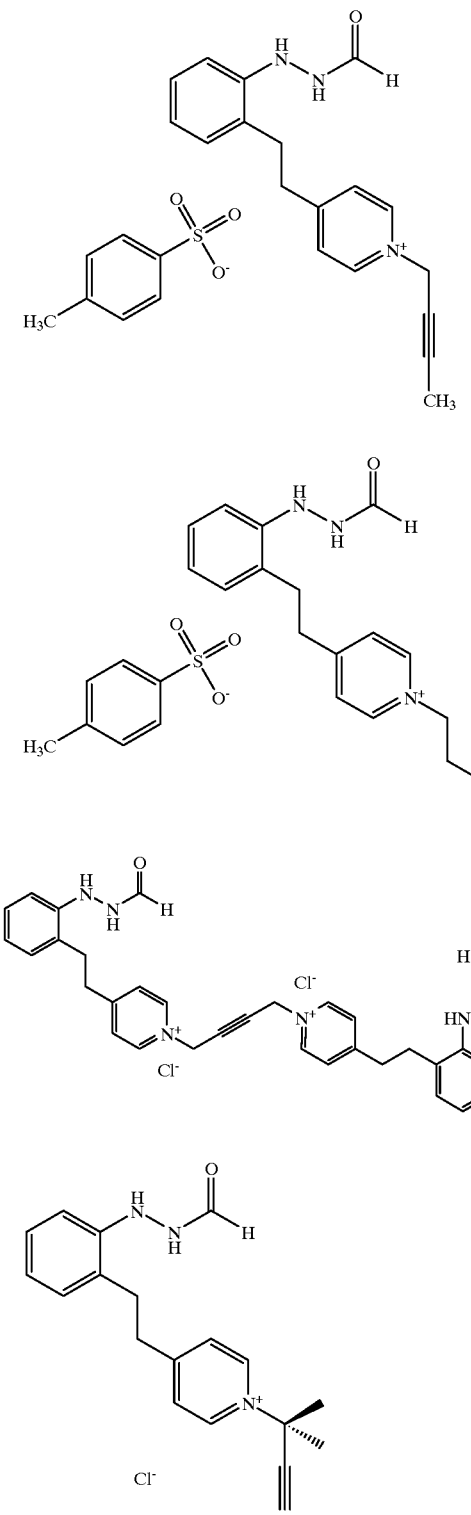
6
-continued
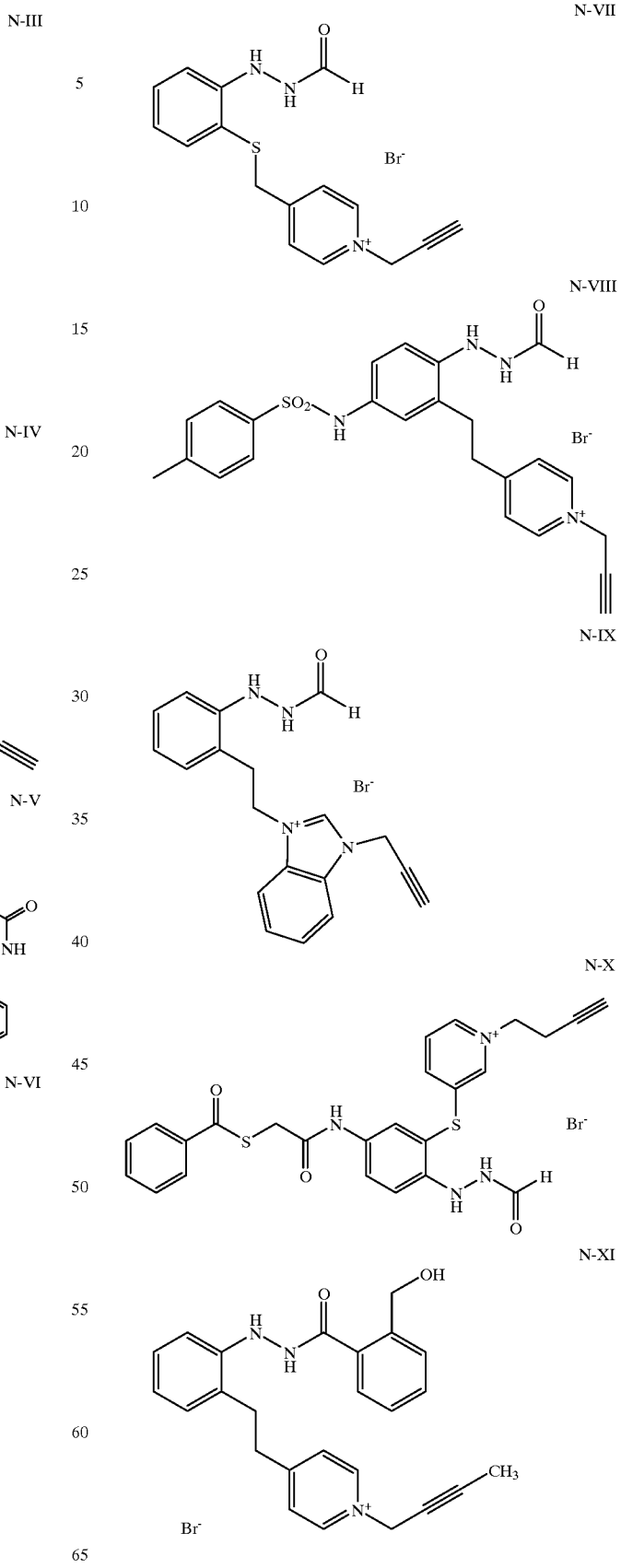

The nucleating agents of the present invention can be prepared using conventional synthetic strategies, know to those skilled in the art. The synthesis of some representative examples will be explained in detail.

The synthesis of nucleating agent N-I:

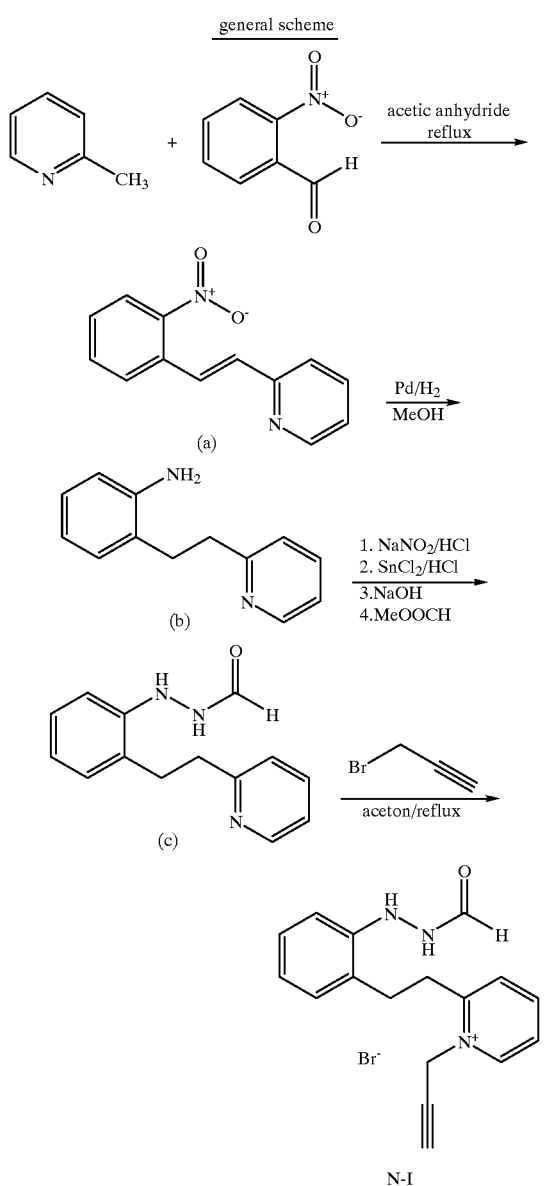

The synthesis of intermediate (a):

A mixture of 50.4 ml (0.5 mol) of 2-methyl-pyridine and 75.6 g (0.5 mol) of o.-nitro-benzaldehyde in 141 ml of acetic anhydride was refluxed for 45 hours. The reaction mixture was allowed to cool down and pourred into 500 ml of ice-water. The crude product was isolated by filtration and washed with 400 ml of water and 60 ml of a 10% NaHCO3-solution. The residual product was dissolved in 700 ml of methylenechloride and filtered over silica. The solvent was removed under reduced pressure and the residue was crystallized from ethanol. (70.8 g, 63%)

The synthesis of intermediate (b):

70.8 g of intermediate (a) in 700 ml of MeOH was hydrogenated with Pd on activated charcoal as catalyst. The catalyst was removed by filtration and the methanol was evaporated under reduced pressure. The oily residue was treated with 100 ml of hexane. Intermediate (b) crystallized with some difficulty. The compound was recrystallized from t.-butyl-methyl-ether/hexane 1/1. (52.5 g, 85%)

The synthesis of intermediate (c):[2]

52.5 g intermediate (b) was dissolved in 122 ml of concentrated hydrochloric acid and 30 g of ice. The mixture was cooled below 0° C. and a solution of 18.3 g of $NaNO_2$ in 30 ml of water was added, while the temperature was kept below 0° C. The reaction was allowed to continue for half an hour at −4° C. A solution of 239 g of $SnCl_2.2H_2O$ in 132 ml of concentrated hydrochloric acid and 60 ml of water was added over 40 minutes, while the temperature was kept below 0° C. The reaction was allowed to continue for 15 minutes at 5° C. The reaction mixture was neutrallized with 10 N NaOH and extracted with 1 liter of methylenechloride. The methylenechloride was washed with 1.5 liter of water. The pooled water fractions were extracted with 1 liter of water. The pooled methylenechloride fractions were dried over $MgSO_4$ and evaporated under reduced pressure. The oily residue was treated with 50 ml of hexane. The crude hydrazine precipitated from the medium and was isolated by filtration. The crude hydrazine was refluxed in 120 ml of methyl formate and 5 ml of dimethyl formamide for 8 hours. The solvent was evaporated under reduced pressure and the oily residue was treated with 300 ml of water. The hydrazide (c) precipitated and was isolated by filtration. The crude hydrazide was recrystallized from ethyl acetate and treated with 150 ml of hexane and 50 ml of t.-butyl-methyl-ether. (44 g, 69%)

The synthesis of nucleating agent N-I:

14.5 g of the hydrazide (c) was dissolved in 120 ml of acetone. 46.8 ml of propargylbromide was added and the mixture was refluxed for 7 hours. Nucleating agent N-I precipitated from the medium, was treated with 500 ml of acetone and 50 ml of MeOH and finally recrystallized from a MeOH/EtOH-mixture. (12 g, 56%).

The synthesis of nucleating agent N-II:

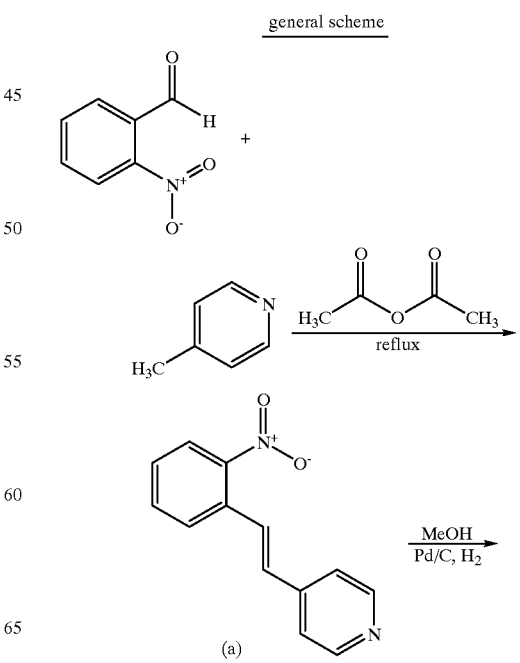

-continued

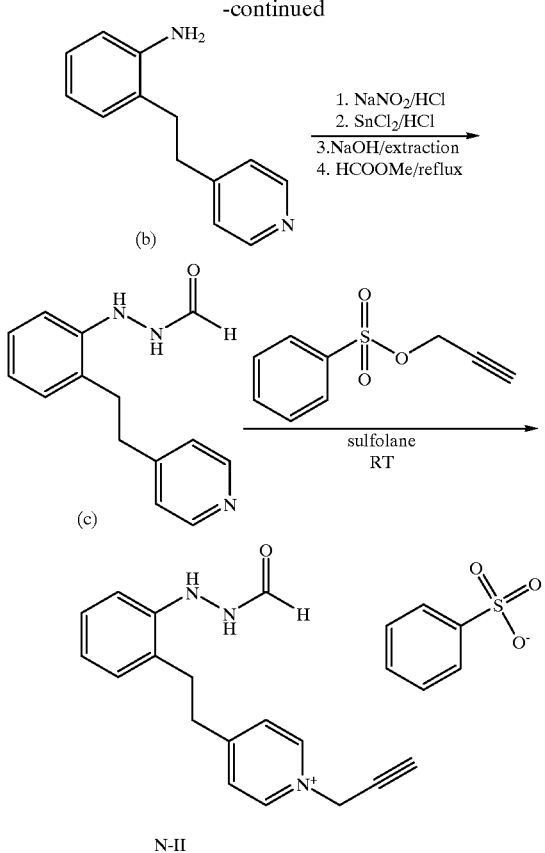

The synthesis of intermediate (a):

143 g (0.95 mol) of 2-nitro-benzaldehyde was dissolved in 178 ml of acetic anhydride. 88 g (0.95 mol) of 4-methylpyridine was added and the reaction mixture was refluxed for 12 hours. The mixture was pourred into 600 g of ice and neutralized with a 10 N NaOH-solution. The intermediate (a) precipitated from the medium. The product was isolated by filtration and washed with water. The crude product was used without further purification (195 g, 91%)

The synthesis of intermediate (b):

195 g (0.86 mol) of intermediate (a) was dissolved in 1300 ml of methanol. 5 g of Pd on activated charcoal was added. Compound (a) was hydrogenated at 45° C. and 54 bar pressure for one and a half hour. The catalyst was removed by filtration and the solvent was removed under reduced pressure. The crude product was purified by preparative column chromatography (eluent:ethyl acetate) (102 g, 60%)

The synthesis of intermediate (c):

101 g (0.509 mol) of intermediate (b) was suspended in 211 ml of concentrated hydrochloric acid. 240 ml of water was added and the reaction mixture was cooled to $-5°$ C. A solution of 37.4 g (0.54 mol) of $NaNO_2$ in 120 ml of water was added while the temperature was kept below 0° C. The precipitated product gradually dissolved. After complete dissolution, the reaction was allowed to continue for half an hour. 695 g (3.08 mol) of $SnCl_2.2H_2O$ in 580 ml of concentrated hydrochloric acid was added. The reaction was allowed to continue over night at room temperature. The reaction mixture was neutralized with 10 N NaOH and extracted 3 times with methylenechloride. The pooled methylenechloride fractions were dried over $Na_2SO_4$. and evaporated under reduced pressure. The oily residue was dissolved in 400 ml methyl formate and refluxed for 16 hours. The hydrazide (c) precipitated from the medium, was isolated by filtration and finally purified by preparative column chromatography (60 g, 49%).

The synthesis of nucleating agent N-II:

46 g (0.19 mol) hydrazide (c) was dissolved in 460 ml of sulfolane. 57 g (0.29 mol) of propargyl benzenesulfonate was added and the reaction was allowed to continue for 48 hours at room temperature. The mixture was pourred into 1600 ml of acetone and allowed to stand for four hours at room temperature. Nucleating agent N-II gradually precipitated from the medium. N-II was isolated by filtration and dried under reduced pressure. (57 g, 69%)

The hydrazides used in accordance with the present invention can be incorporated in the emulsion layer(s) as organic solvent solutions, preferably as methanolic solution.

The nucleating hydrazine compounds of the present invention are preferably incorporated into the emulsion layer but, alternatively, they can be present in an adjacent hydrophylic layer.

We will now explain in detail the most important other features of the photographic material according to the present invention.

Suitable organic resin supports for use in accordance with the present invention include cellulose nitrate film, cellulose acetate film, poly(vinyl acetal) film, polystyrene film, poly(ethylene terephthalate) film, polycarbonate film, polyvinylchloride film or polyolefin films such as polyethylene or polypropylene film. The thickness of such organic resin film is preferably comprised between 0.025 and 0.25 mm.

In a most preferred embodiment the support is a polyethylene terephthalate support, optionally provided with a subbing layer. An example of a suitable subbing layer is a layer containing a polymer containing covalently bound chlorine. Suitable chlorine containing polymers are e.g. polyvinyl chloride, polyvinylidene chloride, a copolymer of vinylidene chloride, an acrylic ester and itaconic acid, a copolymer of vinyl chloride and vinylidene chloride, a copolymer of vinyl chloride, vinylidene chloride and itaconic acid, a copolymer of vinyl chloride, vinyl acetate and vinyl alcohol, A preferred chlorine containing polymer is co(vinylidenechloride-methylacrylate-itaconic acid ; 88% /10% /2%). A most suitable subbing layer contains the latter polymer and a colloidal silica such as KIESELSOL 100F (Bayer AG). Optionally to this composition can be added co(methylacrylate-butadiene-itaconic acid) (49/49/2), preferably in a ratio of about 10 %. The most favourable adhesion properties are obtained when a subbing layer as described above provided with an additional primer layer containing gelatin (preferably 0.25–0.35 g/m²), Kieselsol 300 F (0.30–0.40 g/m²) and a matting agent on the base of polymethylmethacrylate (average size 2 à 3 mm) at a coverage of about 0.001 g/m².

The silver halide emulsion or mixture of emulsions of the photographic material in connection with the present invention can be incorporated in one single layer but, alternatively, a double emulsion layer or even a multiple layer pack can be applied.

The halide composition of the silver halide emulsions used in accordance with the present invention is not specifically limited and may be any composition selected from e.g. silver chloride, silver bromide, silver iodide, silver chlorobromide, silver bromoiodide, and silver chlorobromoiodide. In a prefered embodiment however, the photographic material is a graphic arts material, most preferably, a graphic arts recording material, which by definition is suited for the recording of screened images, linework and/or text, and/or printed circuit board patterns, electronically stored in an image-setter or scanner. Graphic arts recording materials preferably use emulsions containing a majority of chloride, preferably between 50 mole % and 95 mole %, most preferably between 65 mole % and 89 mole %, and a low amount of iodide, the remaining halide being bromide.

The photographic emulsion(s) can be prepared from soluble silver salts and soluble halides according to different methods as described e.g. by P. Glafkidès in "Chimie et Physique Photographique", Paul Montel, Paris (1967), by G. F. Duffin in "Photographic Emulsion Chemistry", The Focal Press, London (1966), and by V. L. Zelikman et al in "Making and Coating Photographic Emulsion", The Focal Press, London (1966). They can be prepared by mixing the halide and silver solutions in partially or fully controlled conditions of temperature, concentrations, sequence of addition, and rates of addition. The silver halide can be precipitated according to the single-jet method, the double-jet method, the conversion method or an alternation of these different methods.

The silver halide particles of the photographic emulsion (s) may have a regular crystalline form such as a cubic or octahedral form or they may have a transition form. They may also have an irregular crystalline form such as a spherical form or a tabular form, or may otherwise have a composite crystal form comprising a mixture of said regular and irregular crystalline forms.

The silver halide grains may have a multilayered grain structure. According to a simple embodiment the grains may comprise a core and a shell, which may have different halide compositions and/or may have undergone different modifications such as the addition of dopes. Besides having a differently composed core and shell the silver halide grains may also comprise different phases inbetween.

Two or more types of silver halide emulsions that have been prepared differently can be mixed for forming a photographic emulsion for use in accordance with the present invention.

The average size of the silver halide grains may range from 0.05 to 1.0 micron, preferably from 0.2 to 0.5 micron. The size distribution of the silver halide particles can be homodisperse or heterodisperse.

The silver halide emulsions can be doped with various metal salts or complexes such as Rhodium and Iridium dopants.

The emulsion can be desalted in the usual ways e.g. by dialysis, by flocculation and re-dispersing, or by ultrafiltration.

The light-sensitive silver halide emulsions are preferably chemically sensitized as described e.g. in the above-mentioned "Chimie et Physique Photographique" by P. Glafkidès, in the above-mentioned "Photographic Emulsion Chemistry" by G. F. Duffin, in the above-mentioned "Making and Coating Photographic Emulsion" by V. L. Zelikman et al, and in "Die Grundlagen der Photographischen Prozesse mit Silberhalogeniden" edited by H. Frieser and published by Akademische Verlagsegesellschaft (1968). As described in said literature chemical sensitization can be carried out by effecting the ripening in the presence of small amounts of compounds containing sulphur e.g. thiosulphate, thiocyanate, thioureas, sulphites, mercapto compounds, and rhodamines. The emulsions can be sensitized also by means of gold-sulphur ripeners, gold-selenium ripeners or by means of reductors e.g. tin compounds as described in GB 789,823, amines, hydrazine derivatives, formamidine-sulphinic acids, and silane compounds. Chemical sensitization can also be performed with small amounts of Ir, Rh, Ru, Pb, Cd, Hg, Tl, Pd, Pt, or Au. One of these chemical sensitization methods or a combination thereof can be used.

The light-sensitive silver halide emulsions can be spectrally sensitized with proper dyes such as those described by F. M. Hamer in "The Cyanine Dyes and Related Compounds", 1964, John Wiley & Sons. Dyes that can be used for the purpose of spectral sensitization include cyanine dyes, merocyanine dyes, complex cyanine dyes, complex merocyanine dyes, hemicyanine dyes, styryl dyes and hemioxonol dyes. Particularly valuable dyes are those belonging to the cyanine dyes, merocyanine dyes ard complex merocyanine dyes.

The silver halide emulsion(s) for use in accordance with the present invention may comprise compounds preventing the formation of fog or stabilizing the photographic characteristics during the production or storage of photographic elements or during the photographic treatment thereof. Many known compounds can be added as fog-inhibiting agent or stabilizer to the silver halide emulsion. Suitable examples are e.g. the heterocyclic nitrogen-containing compounds such as benzothiazolium salts, nitroimidazoles, nitrobenzimidazoles, chlorobenzimidazoles, bromobenzimidazoles, mercaptothiazoles, mercaptobenzothiazoles, mercaptobenzimidazoles, mercaptothiadiazoles, aminotriazoles, benzotriazoles, nitrobenzotriazoles, mercaptotetrazoles, mercaptopyrimidines, mercaptotriazines, benzothiazoline-2-thione, oxazoline-thione, triazaindenes, tetrazaindenes and pentazaindenes, especially those described by Birr in Z. Wiss. Phot. 47 (1952), pages 2–58, triazolopyrimidines such as those described in GB 1,203,757, GB 1,209,146, JA-Appl. 75-39537, and GB 1,500,278, and 7-hydroxy-s-triazolo-[1,5-a]-pyrimidines as described in U.S. Pat. No. 4,727,017, and other compounds such as benzenethiosulphonic acid, benzenethiosulphinic acid and benzenethiosulphonic acid amide. Other compounds that can be used as fog-inhibiting compounds are metal salts such as e.g. mercury or cadmium salts and the compounds described in Research Disclosure N° 17643 (1978), Chapter VI.

The fog-inhibiting agents or stabilizers can be added to the silver halide emulsion prior to, during, or after the ripening thereof and mixtures of two or more of these compounds can be used.

Besides the silver halide another essential component of a light-sensitive emulsion layer is the binder. The binder is a hydrophilic colloid, preferably gelatin. Gelatin can, however, be replaced in part or integrally by synthetic, semi-synthetic, or natural polymers. Synthetic substitutes for gelatin are e.g. polyvinyl alcohol, poly-N-vinyl pyrrolidone, polyvinyl imidazole, polyvinyl pyrazole, polyacrylamide, polyacrylic acid, and derivatives thereof, in particular copolymers thereof. Natural substitutes for gelatin are e.g. other proteins such as zein, albumin and casein, cellulose, saccharides, starch, and alginates. In general, the semi-synthetic substitutes for gelatin are modified natural products e.g. gelatin derivatives obtained by conversion of gelatin with alkylating or acylating agents or by grafting of polymerizable monomers on gelatin, and cellulose derivatives such as hydroxyalkyl cellulose, carboxymethyl cellulose, phthaloyl cellulose, and cellulose sulphates.

The binders of the photographic element, especially when the binder used is gelatin, can be hardened with appropriate hardening agents such as those of the epoxide type, those of the ethylenimine type, those of the vinylsulfone type e.g. 1,3-vinylsulphonyl-2-propanol, chromium salts e.g. chromium acetate and chromium alum, aldehydes e.g. formaldehyde, glyoxal, and glutaraldehyde, N-methylol compounds e.g. dimethylolurea and methyloldimethylhydantoin, dioxan derivatives e.g. 2,3- dihydroxy-dioxan, active vinyl compounds e.g. 1,3,5-triacryloyl-hexahydro-s-triazine, active halogen compounds e.g. 2,4-dichloro-6-hydroxy-s-triazine, and mucohalogenic acids e.g. mucochloric acid and mucophenoxychloric acid. These hardeners can be used alone or in combination. The binders can also be hardened with fast-reacting hardeners such as carbamoylpyridinium salts as disclosed in U.S. Pat. No. 4,063,952.

The photographic material of the present invention may further comprise various kinds of surface-active agents in the photographic emulsion layer or in another hydrophilic colloid layer. Suitable surface-active agents include non-ionic agents such as saponins, alkylene oxides e.g. polyethylene glycol, polyethylene glycol/polypropylene glycol condensation products, polyethylene glycol alkyl ethers or polyethylene glycol alkylaryl ethers, polyethylene glycol esters, polyethylene glycol sorbitan esters, polyalkylene glycol alkylamines or alkylamides, silicone-polyethylene oxide adducts, glycidol derivatives, fatty acid esters of polyhydric alcohols and alkyl esters of saccharides; anionic agents comprising an acid group such as a carboxy, sulpho, phospho, sulphuric or phosphoric ester group; ampholytic agents such as aminoacids, aminoalkyl sulphonic acids, aminoalkyl sulphates or phosphates, alkyl betaines, and amine-N-oxides; and cationic agents such as alkylamine salts, aliphatic, aromatic, or heterocyclic quaternary ammonium salts, aliphatic or heterocyclic ring-containing phosphonium or sulphonium salts. Other suitable surfactants include perfluorinated compounds. Such surface-active agents can be used for various purposes e.g. as coating aids, as compounds preventing electric charges, as compounds improving slidability, as compounds facilitating dispersive emulsification, as compounds preventing or reducing adhesion, and as compounds improving the photographic characteristics e.g higher contrast, sensitization, and development acceleration.

Beside the light sensitive emulsion layer(s) the photographic material can contain several non light sensitive layers, e.g. an anti-stress top layer, one or more backing layers, and one or more intermediate layers eventually containing filter- or antihalation dyes that absorb scattering light and thus promote the image sharpness. Suitable light-absorbing dyes are described in i.a. U.S. Pat. No. 4,092,168, U.S. Pat. No. 4,311,787 and DE 2,453,217. One or more backing layers can be provided at the non-light sensitive side of the support. This layers which can serve as anti-curl layer can contain i.a. matting agents e.g. silica particles, lubricants, antistatic agents, light absorbing dyes, opacifying agents, e.g. titanium oxide and the usual ingredients like hardeners and wetting agents.

The backing layer(s) may further contain an antistatic agent. Suitable antistatic polymers for incorporation in a backing layer are disclosed in e.g. Research Disclosure, April 1990, Item 31237. Further references on ionic conductive polymers include U.S. Pat. No. 4,585,730, U.S. Pat. No. 4,701,403, U.S. Pat. No. 4,589,570, U.S. Pat. No. 5,045,441, EP-A-391 402 and EP-A-420 226. An antistatic agent can also be incorporated in a separate layer or in a subbing layer. Relatively recently electrically conducting conjugated polymers have been developed that have electronic conductivity. For ecological reasons the coating of antistatic layers should proceed where possible from aqueous solutions by using as few as possible organic solvents. The production of antistatic coatings from aqueous coating compositions being dispersions of polythiophenes in the presence of polyanions is described in EP 0 440 957.

The photographic elements in connection with the present invention may further comprise various other additives such as e.g. compounds improving the dimensional stability of the photographic element, UV-absorbers, spacing agents and plasticizers.

Suitable additives for improving the dimensional stability of the photographic elements are e.g. dispersions of a water-soluble or hardly soluble synthetic polymer e.g. polymers of alkyl(meth)acrylates, alkoxy(meth)acrylates, glycidyl (meth)acrylates, (meth)acrylamides, vinyl esters, acrylonitriles, olefins, and styrenes, or copolymers of the above with acrylic acids, methacrylic acids, α-β-unsaturated dicarboxylic acids, hydroxyalkyl (meth)acrylates, sulphoalkyl (meth)acrylates, and styrene sulphonic acids.

Spacing agents can be present, preferably in the top protective layer. In general the average particle size of such spacing agents is comprised between 0.2 and 10 micron. They can be soluble or insoluble in alkali. Alkali-insoluble spacing agents usually remain permanently in the photographic element, whereas alkali-soluble spacing agents usually are removed therefrom in an alkaline processing bath. Suitable spacing agents can be made e.g. of poly (methylmethacrylate), of copolymers of acrylic acid and methylmethacrylate, and of hydroxypropylmethyl cellulose hexahydrophthalate. Other suitable spacing agents have been described in U.S. Pat. No. 4,614,708.

The photographic materials according to the present invention can, after proper exposure, be processed by any means or any chemicals known in the art depending on their particular application. Preferably however, they are processed in so-called "Rapid Access" chemicals, comprising a conventional Phenidone/hydroquinone developing solution or an ascorbic acid developing solution, and a conventional sodium- or ammonium thiosulphate containing fixing solution. As explained above their is no need for special "hard dot Rapid Access" developers, although in principle the materials of the present invention can be developed therein. The development time is usually between 10 and 30 seconds at a temperature of about 35° C.

The present invention will now be illustrated by the following examples without however being limited thereto.

EXAMPLE 1

Preparation of the emulsion

To an aqueous gelatin solution containing sodium chloride, an aqueous solution of silver nitrate and an aqueous halide solution containing potassium bromide, sodium chloride, $2.3 \times 10^{-7}$ mol/mol silver of $Na_3RhCl_6$ and $3.2 \times 10^{-7}$ mol/mol silver of $K_4IrCl_6$ were added with stirring in accordance with a double jet method to form silver chlorobromide grains having an average grain size of 0.27 μm (variation coefficient: 19%) and a chloride content of 64 mol %. These grains were stabilized with minor amounts of potassium iodide.

Thereafter, the emulsion was washed using a conventional flocculation method, and then redispersed with 27 g of gelatin per mol of silver. The resulting emulsion was adjusted to pH 5.0 and then chemically sensitized at 50° C. by adding 6 mg/mol silver of trichloroauric acid and 10 mg/mol silver of sodium thiosulfate and digesting for three hours. The emulsion was stabilized with $9.0 \times 10^{-3}$ mol/mol silver of 4-hydroxy-6-methyl-1,3,3a,7-tetraazaindene, and finally spectrally sensitized with dye D-I. When present the nucleating agents were added as methanol solutions at a concentration of 1 to $8 \times 10^{-3}$ mol/mol silver. Four samples were prepared: 2 invention samples containing invention compound N-1 at two different concentrations, a comparison sample containing prior art hydrazide C-1, and a control sample without hydrazide.

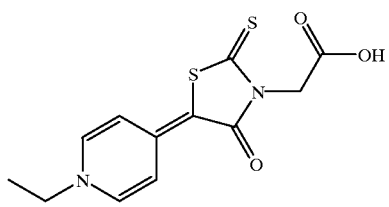

D-I

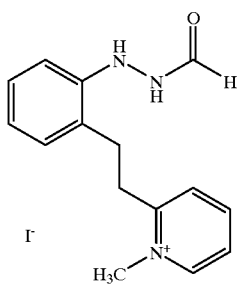

C-I

Preparation of the coated samples

The emulsions were coated onto a polyethylene terephthalate film support at 4 g of silver per square meter and were overcoated with a gelatinous protective layer containing formaldehyde as hardening agent, 50 mg per square meter of 1-p-carboxy-phenyl-3-pyrazolidone, 2.5 mg per square meter of a fluorine-containing surfactant and 10 mg per square meter of poly(methylmethacrylate) matting agent. After coating the film samples were dried.

Exposure and Photographic Processing

Each sample was exposed by means of a xenon flash lamp (light emitting time: $10^{-5}$ s.) through both a step wedge and a filter having its peak of transmittance at 488 nm, and then developed for 30 seconds at 35° C. with Developer A. Thereafter, it was subjected successively to fixation in a conventional ammonium thiosulphate containing fixation bath, and washing and drying operations. The processing took place in a RAPILINE 66T3 processor (Agfa-Gevaert N.V.).

Developer A

|   |   |
|---|---|
| Potassium carbonate | 17.0 g. |
| Potassium hydroxide | 5.3 g. |
| Potassium sulfite | 49.2 g. |
| Hydroquinone | 20.0 g. |
| 1-phenyl-3-pyrazolidone | 0.48 g. |
| Potassium bromide | 10.0 g. |
| 1-phenyl-5-mercaptotetrazole | 0.03 g. |
| Water to make | 1 l. |

The pH of Developer A was adjusted to 10.5 with potassium hydroxide.

Evaluation of Image Contrast

As indication of the contrast of an image the gamma value γ was defined as the slope of a straight line connecting two points on the sensitometric curve, namely those corresponding to (fog+density 3.0) and (fog+density 3.8) (gamma shoulder). The sensitometric data of the samples developed in developer A are represented in table 1.

TABLE 1

| Nucleator | Concentration (mmole/mole Ag) | Fog | γ | Note |
|---|---|---|---|---|
| None | — | 3 | 7.2 | Comparison |
| Compound C-I | 4.0 | 3 | 8.5 | Comparison |
| Compound N-I | 2.0 | 3 | 12.2 | Invention |
| Compound N-I | 4.0 | 3 | 13.7 | Invention |

Evaluation of the dot quality on an Ar laser.

Each sample was exposed on a Crosfield-scanner equipped with an Ar laser leading to a 50%-dot pattern after developing in Developer A, fixing, washing and drying in a RAPILINE 66T3 (registered trademark of Agfa-Gevaert N.V.) processor. The dot quality was evaluated with a magnifying glass in order to examine them for definition and smoothness. Grade 1 represents a poor, fuzzy, "rapid Access" type dot. Grade 5 represents an excellent, hard "lith" type dot. As already mentioned normal hydrazides show also an important image spread leading to considerable dot-growth in function of exposure-intensity or time of development. This leads at exact rendering to a fuzzy quality of the small dots like 4%-dot or less. Besides an excellent image quality a high gradation leads also to a high Dmax at excact rendering. The results are summarized in table 2.

TABLE 2

| Nucleator | Conc. (mmole per mole Ag) | Dmax | Dot Qual. | Dot Qual. of 4%-dot at exact rendering | Note |
|---|---|---|---|---|---|
| None | — | 4.8 | 1 | 1 | Comparison |
| Compound C-I | 4.0 | 5.0 | 4 | 2 | Comparison |
| Compound N-I | 4.0 | 5.4 | 4 | 4 | Invention |

The sample containing the compound of this invention clearly demonstrates "lith" type dot characteristics, a higher density at exact rendering and a better quality of the 4%-dot as compared to the film sample without the nucleator or the sample with the nucleator not containing a Q group according to the invention (compound C-I).

EXAMPLE 2

Preparation of the emulsion.

The preparation of the emulsions was completely similar to example 1 with the exception that dye D-II was used as spectral sensitizer.

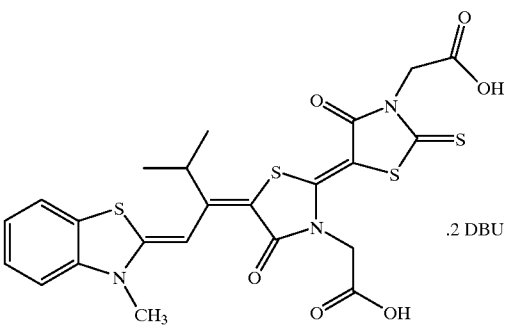

D-II

The coating of the samples and the processing proceeded exactly as for example 1. The exposure was similar to example 1 with the exception that a filter having a maximal transmittance at 622 nm was used.

Evaluation of Image Contrast.

The sensitometric data of the samples developed in developer A are included in table 3.

TABLE 3

| Nucleator | Concentration (mmole/mole Ag) | γ | Note |
| --- | --- | --- | --- |
| None | — | 7.9 | Comparison |
| Compound C-I | 2.0 | 2.9 | Comparison |
| Compound N-I | 2.0 | 7.3 | Invention |
| Compound N-I | 4.0 | 9.8 | Invention |
| Compound N-II | 1.5 | 15.1 | Invention |
| Compound N-II | 3.0 | 18.1 | Invention |
| Compound N-III | 4.0 | 13.9 | Invention |
| Compound N-IV | 2.0 | 18.5 | Invention |

The compounds of this invention clearly demonstrate an important increase in contrast at high density in contrast to the compound without a propargyllic group leading to enhanced image quality for graphic applications.

Evaluation of the dot quality on a red laserdiode.

The samples were exposed on an image-setter ACCUSET 1000 (Agfa) equipped with a red laserdiode leading to a 50%-dot pattern after developing in Developer A, fixing, washing and drying in a RAPILINE 66T3 (Agfa) processor. The dot quality was evaluated with a magnifying glass in order to examine them for definition and smoothness. Grade 1 represents a poor, fuzzy, "rapid Access" type dot. Grade 5 represents an excellent, hard "lith" type dot. Beside an excellent image quality a high gradation leads also to a high Dmax at exact rendering. The results are summarized in table 4.

TABLE 4

| Nucleator | Concentration (mmole/mole Ag) | Dot Quality | Dot quality of 4%-dot at exact rendering | Dmax | Note |
| --- | --- | --- | --- | --- | --- |
| None | — | 1 | 1 | 3.3 | Comparison |
| Compound C-I | 2.0 | 4 | 3 | 3.8 | Comparison |
| Compound N-I | 4.0 | 4 | 4 | 3.8 | Invention |
| Compound N-II | 3.0 | 5 | 5 | 4.7 | Invention |
| Compound N-III | 4.0 | 5 | 4 | 3.7 | Invention |
| Compound N-IV | 2.0 | 4 | 5 | 4.0 | Invention |

The samples containing the compounds of this invention clearly demonstrate "lith" type dot characteristics, a higher density at exact rendering as compared to the sample without nucleator, and a better quality of the small 4%-dot as compared to the film sample with the nucleator not containing the specific Q group according to the present invention (compound C-I).

We claim:

1. Photographic material comprising a support, at least one emulsion layer, and optionally one or more other hydrophilic layers, characterized in that said emulsion layer or another hydrophilic layer adjacent to said emulsion layer contains a compound according to general formula I:

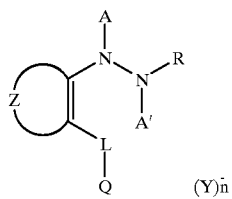

Formula I or a dimeric form of said formula I, wherein

1) R represents an acyl-group selected from the group consisting of $COR^1$, $SO_2R^2$, $SOR^3$, $POR^4R^5$ and $COCOR^6$; each of $R^1$ and $R^6$ independently represents hydrogen, a substituted or unsubstituted alkyl group, a substituted or unsubstituted aryl- or heteroarylgroup, $OR^7$, or $NR^8R^9$; each of $R^2$ and $R^3$ independently represents a substituted or unsubstituted alkylgroup, a substituted or unsubstituted aryl- or heteroarylgroup, $OR^7$ or $NR^8R^9$; each of $R^4$ and $R^5$ indepedently represents one of the significances given for $R^2$ or they may constitute together the necessary atoms to close a ring; $R^7$ represents a substituted or unsubstituted alkylgroup, a substituted or unsubstituted aryl- or heteroarylgroup; each of $R^8$ and $R^9$ independently represents hydrogen, a substituted or unsubstituted alkylgroup or a substituted or unsubstituted aryl- or heteroarylgroup or they may constitute together the necessary atoms to form a ring;

2) each of A and A' independently represent a hydrogen, a group capable of yielding hydrogen under alkaline photographic processing conditions or a $SO_2R^{10}$-group, provided that, if A is a $SO_2R^{10}$, A' is a hydrogen and vice versa; $R^{10}$ has one of the significances given for $R^2$;

3) L is a divalent linking group;

4) Q is an aromatic heterocyclic ring containing a quaternary nitrogen atom which is substituted by a substituted or unsubstituted aliphatic chain comprising at least one carbon—carbon triple bond;

5) Y⁻ is a negatively charged counterion to compensate the positive charge of Q;

n is 0 if the compound according to formula I is an inner salt or an integer equal to the positive charge of Q, and 6) Z represents the necessary atoms to form a substituted or unsubstituted aromatic or heteroaromatic ring.

2. Photographic material according to claim 1 wherein said aromatic heterocyclic ring of Q is a substituted or unsubstituted pyridinium group.

3. Photographic material according to claim 1 wherein said aliphatic chain present in Q is a propargyllic group or a butynyl group.

4. Photographic material according to claim 1 wherein said divalent linking group L is a substituted or unsubstituted ethylene group.

5. A compound according to general formula I

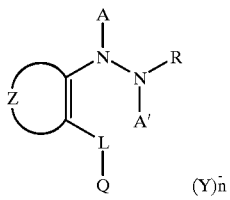

Formula I or a dimeric form of said formula I, wherein
1) R represents an acyl-group selected from the group consisting of $COR^1$, $SO_2R^2$, $SOR^3$, $POR^4R^5$ and $COCOR^6$; each of $R^1$ and $R^6$ independently represents hydrogen, a substituted or unsubstituted alkyl group, a substituted or unsubstituted aryl- or heteroarylgroup, $OR^7$, or $NR^8R^9$; each of $R^2$ and $R^3$ independently represents a substituted or unsubstituted alkylgroup, a substituted or unsubstituted aryl- or heteroarylgroup, $OR^7$ or $NR^8R^9$; each of $R^4$ and $R^5$ indepedently represents one of the significances given for $R^2$ or they may constitute together the necessary atoms to close a ring; $R^7$ represents a substituted or unsubstituted alkylgroup, a substituted or unsubstituted aryl- or heteroarylgroup; each of $R^8$ and $R^9$ independently represents hydrogen, a substituted or unsubstituted alkylgroup or a substituted or unsubstituted aryl- or heteroarylgroup or they may constitute together the necessary atoms to form a ring;
2) each of A and A' independently represent a hydrogen, a group capable of yielding hydrogen under alkaline photographic processing conditions or a $SO_2R^{10}$-group, provided that, if A is a $SO_2R^{10}$, A' is a hydrogen and vice versa; $R^{10}$ has one of the significances given for $R^2$;
3) L is a divalent linking group;
4) Q is an aromatic heterocyclic ring containing a quaternary nitrogen atom which is substituted by a substituted or unsubstituted aliphatic chain comprising at least one carbon—carbon triple bond;
5) $Y^-$ is a negatively charged counterion to compensate the positive charge of Q;
n is 0 if the compound according to formula I is an inner salt or an integer equal to the positive charge of Q, and
6) Z represents the necessary atoms to form a substituted or unsubstituted aromatic or heteroaromatic ring.

6. A compound according to claim 5 wherein said aromatic heterocyclic ring of Q is a substituted or unsubstituted pyridinium group.

7. A compound according to claim 5 wherein said aliphatic chain present in Q is a propargyllic group or a butynyl group.

8. A compound according to claim 5 wherein said divalent linking group L is a substituted or unsubstituted ethylene group.

* * * * *